United States Patent [19]

Onishi et al.

[11] Patent Number: 5,496,824
[45] Date of Patent: Mar. 5, 1996

[54] CYCLOPROPANE DERIVATIVES AND ANTI-VIRAL AGENT CONTAINING THE SAME

[75] Inventors: Tomoyuki Onishi; Chika Mukai; Takaaki Sekiyama; Takashi Tsuji; Satoshi Iwayama; Masahiko Okunishi, all of Kawasaki, Japan

[73] Assignee: Ajinomoto Co., Inc., Tokyo, Japan

[21] Appl. No.: 327,851

[22] Filed: Oct. 21, 1994

[30] Foreign Application Priority Data

Oct. 21, 1993 [JP] Japan ................ 5-263490

[51] Int. Cl.⁶ .................... C07D 239/54; A61K 31/505
[52] U.S. Cl. ........................... 514/274; 544/314
[58] Field of Search ............. 514/274; 544/313, 544/314

[56] References Cited

U.S. PATENT DOCUMENTS 5,342,840  8/1994  Hatsuya et al. ............ 544/276

FOREIGN PATENT DOCUMENTS 0291230  11/1988  European Pat. Off. .
0458363  11/1991  European Pat. Off. .
0484843  5/1992  European Pat. Off. .
0502690  9/1992  European Pat. Off. .

OTHER PUBLICATIONS

Journal of Medicinal Chemistry, vol. 31, No. 12, Dec. 1988, Wallace T. Ashton, et al., "Synthesis and Antiherpetic Activity of (.+-.)-9-[[(Z)-2-(Hydroxymethyl)Cyclopropyl]Methyl]Guanine And Related Compounds", pp. 2304–2315.

Journal of Medicinal Chemistry, vol. 35, No. 10, May 15, 1992, William A. Slusarchyk, et al., "Synthesis And Antiviral of 1–Cyclobutyl–5(2–Bromovinyl)Uracil Nucleoside Analogues And Related Compounds", pp. 1799–1806.

Chung K. Chu et al., "Chemistry and Antiviral Activities of Acyclonucleosides", *J. Heterocyclic Chem.*, Mar.–Apr. 1986, 23–289–319.

*Primary Examiner*—John M. Ford
*Attorney, Agent, or Firm*—Oblon, Spivak, McClelland, Maier & Neustadt

[57] ABSTRACT

The present invention provides a pharmaceutical agent having a high pharmaceutical potency against varicella-zoster viruses and herpes simplex viruses, compositions containing the same, and methods for treating varicella-zoster viruses using the same.

11 Claims, No Drawings

CYCLOPROPANE DERIVATIVES AND ANTI-VIRAL AGENT CONTAINING THE SAME

BACKGROUND OF THE INVENTION

1. Field of the Invention

The present invention relates to novel cyclopropane derivatives having anti-viral activity especially effective against varicella-zoster viruses and herpes simplex viruses, to anti-viral compositions containing the same, and to methods of treating patients having varicella-zoster virus or herpes simplex virus with the same.

2. Discussion of the Background

Varicella-zoster viruses cause varicella in infants with high fever and cause zoster in adults with much pain such as neuralgia, etc. Some anti-viral agents such as acyclovir can be used to treat these viruses, but are not always satisfactory in view of their pharmaceutical potency and unfavorable side-effect (see Am. J. Med., 85, (Suppl. 2A), 116–122 (1988), U.S. Pat. No. 4,386,076, JP-A5/78357).

SUMMARY OF THE INVENTION

Accordingly, one object of the present invention is to provide compounds having high anti-viral potency against varicella-zoster virus and having high safety.

A second object is to provide pharmaceutical compositions containing such compounds.

A third object is to provide methods for treating patients with varicella-zoster virus or herpes simplex virus.

The present inventors have now found that these objects can be achieved with cyclopropane derivatives of the formula (I) which have excellent anti-viral activity against varicella-zoster viruses and herpes simplex viruses.

DETAILED DESCRIPTION OF THE INVENTION

Suitable cyclopropane derivative according to the present invention are of the formula (I):

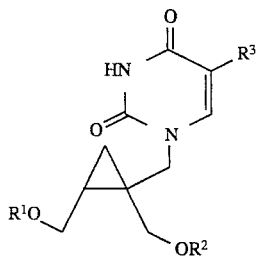

(I)

wherein $R^1$ and $R^2$, the same or different, each represent a hydrogen atom, an acyl group or a substituted acyl group; $R^3$ represents a halogen atom, an $C_{2-5}$ alkyl group, a trifluoromethyl group, a 2-haloalkyl group, a 1-alkenyl group, a 2-halo-1-alkenyl group, or a 1-alkynyl group.

Suitable acyl groups can be derived from fatty acids having 1 to 6 carbon atoms such as formyl, acetyl, propionyl, butyryl, valeryl, isovaleryl, pivalyl, hexanoyl group. The acyl group may be substituted with a $C_{3-8}$ cycloalkyl group such as a cyclohexanecarbonyl group or an $C_{6-8}$ aryl group such as a benzoyl group.

The halogen atom may be fluorine, chlorine, bromine or iodine.

Suitable $C_{2-5}$ alkyl groups include ethyl, propyl, isopropyl, butyl, isobutyl and pentyl group.

Suitable 2-haloalkyl groups are 2-haloalkyl groups having from 2 to 5 carbon atoms such as 2-fluoroethyl, 2-fluoropropyl, 2-chloroethyl, 2-chloropropyl, 2-bromoethyl, 2-bromopropyl, 2-iodoethyl and 2-iodopropyl groups. Especially preferred is 2-chloroethyl or 2-bromoethyl group.

Suitable 1-alkenyl groups are 1-alkenyl groups having 2 to 5 carbon atoms, preferably ethenyl and 1-propenyl. Especially preferred is ethenyl group.

Suitable 2-halo-1-alkenyl groups are 2-halo-1-alkenyl groups having 2 to 5 carbon atoms such as 2-fluoroethenyl, 2-chloroethenyl, 2-bromoethenyl and 2-iodoethenyl groups. Especially preferred are 2-chloroethenyl, 2-bromoethenyl and 2-iodoethenyl group.

Suitable 1-alkynyl groups are 1-alkynyl groups having 2 to 5 carbon atoms, preferably, ethynyl and 1-propynyl group.

Preferred examples of the compounds of the present invention are mentioned below.

1-[1'α,2'α-bis(hydroxymethyl)cyclopropan-1'β-yl]methyl-5-bromo-2,4(1H,3 H)-pyrimidinedione 1-[1'α,2'β-bis(hydroxymethyl)cyclopropan-1'β-yl]methyl-5-bromo-2,4(1H,3 H)-pyrimidinedione 1-[1'α,2'α-bis(hydroxymethyl)cyclopropan-1'β-yl]methyl-5-chloro-2,4(1H,3 H)-pyrimidinedione 1-[1'α,2'β-bis(hydroxymethyl)cyclopropan-1'β-yl]methyl-5-chloro-2,4(1H,3 H)-pyrimidinedione 1-[1'α,2'α-bis(hydroxymethyl)cyclopropan-1'β-yl]methyl-5-fluoro-2,4(1H,3 H)-pyrimidinedione 1-[1'α,2'β-bis(hydroxymethyl)cyclopropan-1'β-yl]methyl-5-fluoro-2,4(1H,3 H)-pyrimidinedione 1-[1'α,2'α-bis(hydroxymethyl)cyclopropan-1'β-yl]methyl-5-iodo-2,4(1H,3 H)-pyrimidinedione 1-[1'α,2'β-bis(hydroxymethyl)cyclopropan-1'β-yl]methyl-5- iodo-2,4(1H,3 H)-pyrimidinedione 1-[1'α,2'α-bis(acetoxymethyl)cyclopropan-1'β-yl]methyl-5-bromo -2,4(1H,3 H)-pyrimidinedione 1-[1'α,2'β-bis(acetoxymethyl)cyclopropan-1'β-yl]methyl-5-bromo -2,4(1H,3 H)-pyrimidinedione 1-[1'α,2'α-bis(acetoxymethyl)cyclopropan-1'β-yl]methyl-5-chloro-2,4(1H,3 H)-pyrimidinedione 1-[1'α,2'β-bis(acetoxymethyl)cyclopropan-1'β-yl]methyl-5-chloro-2,4(1H,3 H)-pyrimidinedione 1-[1'α,2'α-bis(acetoxymethyl)cyclopropan-1'β-yl]methyl-5-fluoro-2,4(1H,3 H)-pyrimidinedione 1-[1'α,2'β-bis(acetoxymethyl)cyclopropan-1'β-yl]methyl-5-fluoro-2,4(1H,3 H)-pyrimidinedione 1-[1'α,2'α-bis(acetoxymethyl)cyclopropan-1'β-yl]methyl-5-iodo-2,4(1H,3 H)-pyrimidinedione 1-[1'α,2'β-bis(acetoxymethyl)cyclopropan-1'β-yl]methyl-5-iodo-2,4(1H,3 H)-pyrimidinedione 1-[1'α,2'α-bis(hydroxymethyl)cyclopropan-1'β-yl]methyl-5-ethyl-2,4(1H,3 H)-pyrimidinedione 1-[1'α,2'β-bis(hydroxymethyl)cyclopropan-1'β-yl]methyl-5-ethyl-2,4(1H,3 H)-pyrimidinedione 1-[1'α,2'α-bis(hydroxymethyl)cyclopropan-1'β-yl]methyl-5-propyl-2,4(1H,3 H)-pyrimidinedione 1-[1'α,2'β-bis(hydroxymethyl)cyclopropan-1'β-yl]methyl-5-propyl-2,4(1H,3 H)-pyrimidinedione 1-[1'α,2'α-bis(acetoxymethyl)cyclopropan-1'β-yl]methyl-5-ethyl-2,4(1H,3 H)-pyrimidinedione 1-[1'α,2'β-bis(acetoxymethyl)cyclopropan-1'β-yl]methyl-5-ethyl-2,4(1H,3 H)-pyrimidinedione 1-[1'α,2'α-bis(acetoxymethyl)cyclopropan-1'β-yl]methyl-5-propyl-2,4(1H,3 H)-pyrimidinedione 1-[1'α,2'β-bis(acetoxymethyl)cyclopropan-1'β-yl]methyl-5-propyl-2,4(1H,3 H)-pyrimidinedione 1-[1'α,2'α-bis(hydroxymethyl)cyclopropan-1'β-yl]methyl-5-trifluoromethyl-2,4(1H,3H)-pyrimidinedione
1-[1'α,2'β-bis(hydroxymethyl)cyclopropan-1'β-yl]methyl-5-trifluoromethyl-2,4(1H,3H)-pyrimidinedione
1-[1'α,2'α-bis(acetoxymethyl)cyclopropan-1'β-yl]methyl-5-trifluoromethyl-2,4(1H,3H)-pyrimidinedione
1-[1'α,2'β-bis(acetoxymethyl)cyclopropan-1'β-yl]methyl-5-trifluoromethyl-2,4(1H,3H)-pyrimidinedione
1-[1'α,2'α-bis(hydroxymethyl)cyclopropan-1'β-yl]methyl-5-(2-bromoethyl)-2,4(1H,3H)-pyrimidinedione
1-[1'α,2'β-bis(hydroxymethyl)cyclopropan-1'β-yl]methyl-5-(2-bromoethyl)-2,4(1H,3H)-pyrimidinedione
1-[1'α,2'α-bis(hydroxymethyl)cyclopropan-1'β-yl]methyl-5-(2-chloroethyl)-2,4(1H,3H)-pyrimidinedione
1-[1'α,2'β-bis(hydroxymethyl)cyclopropan-1'β-yl]methyl-5-(2-chloroethyl)-2,4(1H,3H)-pyrimidinedione
1-[1'α,2'α-bis(hydroxymethyl)cyclopropan-1'β-yl]methyl-5-(2-fluoroethyl)-2,4(1H,3H)-pyrimidinedione
1-[1'α,2'β-bis(hydroxymethyl)cyclopropan-1'β-yl]methyl-5-(2-fluoroethyl)-2,4(1H,3H)-pyrimidinedione
1-[1'α,2'α-bis(hydroxymethyl)cyclopropan-1'β-yl]methyl-5-(2-iodoethyl)-2,4(1H,3H)-pyrimidinedione
1-[1'α,2'β-bis(hydroxymethyl)cyclopropan-1'β-yl]methyl-5-(2-iodoethyl)-2,4(1H,3H)-pyrimidinedione
1-[1'α,2'α-bis(acetoxymethyl)cyclopropan-1'β-yl]methyl-5-(2-bromoethyl)-2,4(1H,3H)-pyrimidinedione
1-[1'α,2'β-bis(acetoxymethyl)cyclopropan-1'β-yl]methyl-5-(2-bromoethyl)-2,4(1H,3H)-pyrimidinedione
1-[1'α,2'α-bis(acetoxymethyl)cyclopropan-1'β-yl]methyl-5-(2-chloroethyl)-2,4(1H,3H)-pyrimidinedione
1-[1'α,2'β-bis(acetoxymethyl)cyclopropan-1'β-yl]methyl-5-(2-chloroethyl)-2,4(1H,3H)-pyrimidinedione
1-[1'α,2'α-bis(acetoxymethyl)cyclopropan-1'β-yl]methyl-5-(2-fluoroethyl)-2,4(1H,3H)-pyrimidinedione
1-[1'α,2'β-bis(acetoxymethyl)cyclopropan-1'β-yl]methyl-5-(2-fluoroethyl)-2,4(1H,3H)-pyrimidinedione
1-[1'α,2'α-bis(acetoxymethyl)cyclopropan-1'β-yl]methyl-5-(2-iodoethyl)-2,4(1H,3H)-pyrimidinedione
1-[1'α,2'β-bis(acetoxymethyl)cyclopropan-1'β-yl]methyl-5-(2-iodoethyl)-2,4(1H,3H)-pyrimidinedione
1-[1'α,2'α-bis(hydroxymethyl)cyclopropan-1'β-yl]methyl-5-ethenyl-2,4(1H,3H)-pyrimidinedione
1-[1'α,2'β-bis(hydroxymethyl)cyclopropan-1'β-yl]methyl-5-ethenyl-2,4(1H,3H)-pyrimidinedione
1-[1'α,2'α-bis(hydroxymethyl)cyclopropan-1'β-yl]methyl-5-[(E)-1-propenyl]-2,4(1H,3H)-pyrimidinedione
1-[1'α,2'β-bis(hydroxymethyl)cyclopropan-1'β-yl]methyl-5-[(E)-1-propenyl]-2,4(1H,3H)-pyrimidinedione
1-[1'α,2'α-bis(acetoxymethyl)cyclopropan-1'β-yl]methyl-5-ethenyl-2,4(1H,3H)-pyrimidinedione
1-[1'α,2'β-bis(acetoxymethyl)cyclopropan-1'β-yl]methyl-5-ethenyl-2,4(1H,3H)-pyrimidinedione
1-[1'α,2'α-bis(acetoxymethyl)cyclopropan-1'β-yl]methyl-5-[(E)-1-propenyl]-2,4(1H,3H)-pyrimidinedione
1-[1'α,2'β-bis(acetoxymethyl)cyclopropan-1'β-yl]methyl-5-[(E)-1-propenyl]-2,4(1H,3H)-pyrimidinedione
1-[1'α,2'α-bis(hydroxymethyl)cyclopropan-1'β-yl]methyl-5-[(E)-2-bromoethenyl]-2,4(1H,3H)-pyrimidinedione
1-[1'α,2'β-bis(hydroxymethyl)cyclopropan-1'β-yl]methyl-5-[(E)-2-bromoethenyl]-2,4(1H,3H)-pyrimidinedione
1-[1'α,2'α-bis(hydroxymethyl)cyclopropan-1'β-yl]methyl-5-[(E)-2-chloroethenyl]-2,4(1H,3H)-pyrimidinedione
1-[1'α,2'β-bis(hydroxymethyl)cyclopropan-1'β-yl]methyl-5-[(E)-2-chloroethenyl]-2,4(1H,3H)-pyrimidinedione
1-[1'α,2'α-bis(hydroxymethyl)cyclopropan-1'β-yl]methyl-5-[(E)-2-fluoroethenyl]-2,4(1H,3H)-pyrimidinedione
1-[1'α,2'β-bis(hydroxymethyl)cyclopropan-1'β-yl]methyl-5-[(E)-2-fluoroethenyl]-2,4(1H,3H)-pyrimidinedione
1-[1'α,2'α-bis(hydroxymethyl)cyclopropan-1'β-yl]methyl-5-[(E)-2-iodoethenyl]-2,4(1H,3H)-pyrimidinedione
1-[1'α,2'β-bis(hydroxymethyl)cyclopropan-1'β-yl]methyl-5-[(E)-2-iodoethenyl]-2,4(1H,3H)-pyrimidinedione
1-[1'α,2'α-bis(acetoxymethyl)cyclopropan-1'β-yl]methyl-5-[(E)-2-bromoethenyl]-2,4(1H,3H)-pyrimidinedione
1-[1'α,2'β-bis(acetoxymethyl)cyclopropan-1'β-yl]methyl-5-[(E)-2-bromoethenyl]-2,4(1H,3H)-pyrimidinedione
1-[1'α,2'α-bis(acetoxymethyl)cyclopropan-1'β-yl]methyl-5-[(E)-2-chloroethenyl]-2,4(1H,3H)-pyrimidinedione
1-[1'α,2'β-bis(acetoxymethyl)cyclopropan-1'β-yl]methyl-5-[(E)-2-chloroethenyl]-2,4(1H,3H)-pyrimidinedione
1-[1'α,2'α-bis(acetoxymethyl)cyclopropan-1'β-yl]methyl-5-[(E)-2-fluoroethenyl]-2,4(1H,3H)-pyrimidinedione
1-[1'α,2'β-bis(acetoxymethyl)cyclopropan-1'β-yl]methyl-5-[(E)-2-fluoroethenyl]-2,4(1H,3H)-pyrimidinedione
1-[1'α,2'α-bis(acetoxymethyl)cyclopropan-1'β-yl]methyl-5-[(E)-2-iodoethenyl]-2,4(1H,3H)-pyrimidinedione
1-[1'α,2'β-bis(acetoxymethyl)cyclopropan-1'β-yl]methyl-5-[(E)-2-iodoethenyl]-2,4(1H,3H)-pyrimidinedione
1-[1'α,2'α-bis(hydroxymethyl)cyclopropan-1'β-yl]methyl-5-(1-propynyl)-2,4(1H,3H)-pyrimidinedione
1-[1'α,2'α-bis(acetoxymethyl)cyclopropan-1'β-yl]methyl-5-(1-propynyl)-2,4(1H,3H)-pyrimidinedione
1-[1'α,2'α-bis(hydroxymethyl)cyclopropan-1'β-yl]methyl-5-ethynyl-2,4(1H,3H)-pyrimidinedione
1-[1'α,2'β-bis(hydroxymethyl)cyclopropan-1'β-yl]methyl-5-ethynyl-2,4(1H,3H)-pyrimidinedione
1-[1'α,2'β-bis(hydroxymethyl)cyclopropan-1'β-yl]methyl-5-(1-propynyl)-2,4(1H,3H)-pyrimidinedione
1-[1'α,2'α-bis(acetoxymethyl)cyclopropan-1'β-yl]methyl-5-ethynyl-2,4(1H,3H)-pyrimidinedione
1-[1'α,2'β-bis(acetoxymethyl)cyclopropan-1'β-yl]methyl-5-ethynyl-2,4(1H,3H)-pyrimidinedione
1-[1'α,2'β-bis(acetoxymethyl)cyclopropan-1'β-yl]methyl-5-(1-propynyl)-2,4(1H,3H)-pyrimidinedione Suitable cyclopropane derivatives of formula (I) include their racemates, optical isomers and stereoisomers. Regarding the relative configuration of each compound, the cyclopropane moiety is considered to be on a flat plane and the substituents positioned below the plane are represented by "α" while those positioned above the plane are represented by "β".

The compounds of the present invention may be prepared, for example, as follows:

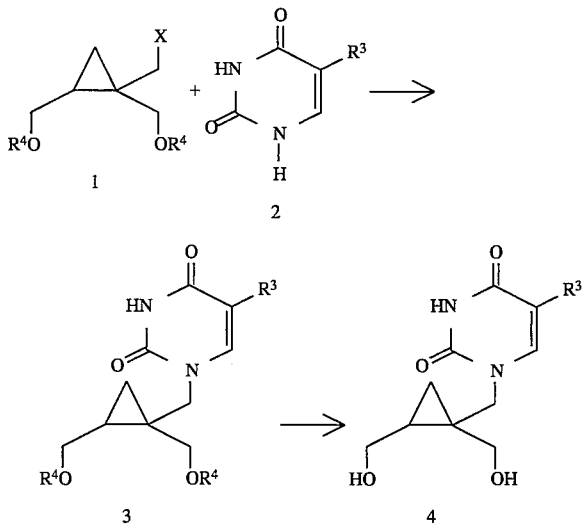

wherein R⁴ represents a protective group for a hydroxyl group; X represents a leaving group such as a p-toluenesulfonyloxy group, methanesulfonyloxy group or a halogen; and $R^3$ has the same meaning as mentioned above.

Suitable protective groups for a hydroxyl group are described by Theodora W. Green in "Protective Groups in Organic Synthesis", John Wiley & Sons: New York, 1981.

Compounds of formula (1) may be prepared according to the method described in Japanese Patent Laid-Open Application No. 5-78357. That is, a compound of the formula (1) can be reacted with a 5-substituted uracil of formula (2) in a polar solvent such as dimethylsulfoxide or dimethylformamide in the presence of a base such as potassium carbonate or sodium hydride, by stirring them under heat, to give a compound of formula (3). In this step, 18-crown-6 may be added to the reaction system. Next, the protective group $R^4$ is removed to obtain a compound of formula (4).

On the other hand, 1-[1'S,2'R-bis(hydroxymethyl)-cyclopropan-1'-yl]methyl-5-[(E)-2-bromoethenyl]-2,4(1H,3H)pyrimidinedione, which is within the scope of the compounds of the present invention, may also be produced according to the following process.

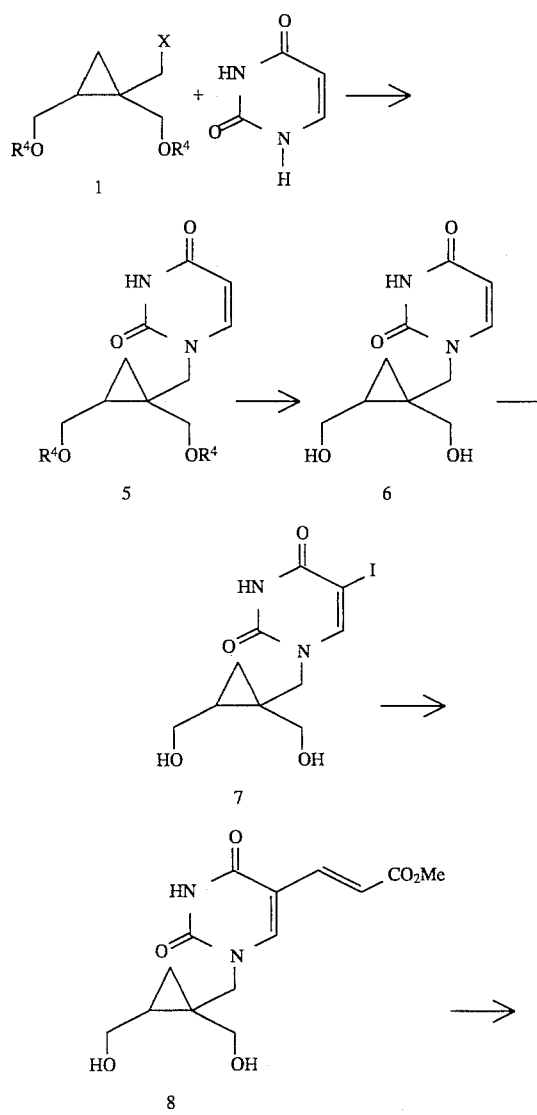

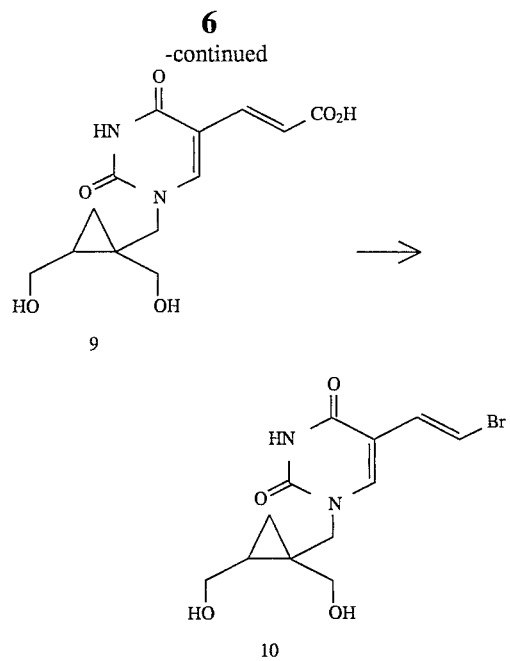

where $R^4$ and X have the same meanings as those mentioned above.

Compounds of formula (1) can be reacted with uracil in a polar solvent such as dimethylsulfoxide, dimethylformamide, in the presence of a base such as potassium carbonate or sodium hydride, by stirring them under heat, to give a compound of formula (5). In this step, 18-crown-6 may be added to the reaction system. Next, the protective group $R^4$ is removed to obtain a compound of formula (6), and this is iodinated by treating it with iodine and an aqueous solution of nitric acid in dioxane, to obtain a compound of formula (7). This is then treated with methyl acrylate in the presence of palladium(II) acetate, triphenylphosphine and triethylamine in dioxane to give a compound of formula (8), which is thereafter saponified at its methyl ester group to obtain a compound of formula (9). The compound of formula (9) thus obtained is treated with N-bromosuccinimide in the presence of potassium bicarbonate or the like in a polar solvent such as dimethylformamide to obtain a compound of formula (10).

Where the compounds of the present invention are used as anti-viral agents, they may be administered to patients by intravenous administration, peroral administration or subcutaneous administration. The dose of the compound varies, depending on the condition and the age of the patient and on how the compound is administered to the patient. In general, the dose is from 0.1 to 500 mg/kg/day.

The compounds of the present invention can be mixed with suitable pharmaceutical carriers to form anti-viral compositions, which can also be administered to patients. Suitable forms of the anti-viral compositions include injectable solutions, tablets, granules, fine granules, powder, capsules, cream, suppositories, etc.

Suitable pharmaceutical carriers include lactose, glucose, D-mannitol, starch, crystalline cellulose, calcium carbonate, kaolin, gelatin, hydroxypropyl cellulose, hydroxypropylmethyl cellulose, polyvinyl pyrrolidone, ethanol, carboxymethyl cellulose, calcium carboxymethyl cellulose, magnesium stearate, talc, acetyl cellulose, white sugar, titanium oxide, benzoic acid, paraoxybenzoate, sodium dehydroacetate, arabic gum, tragacanth, methyl cellulose, egg yolk, surfactants, simple syrup, citric acid, distilled water, glycerin, propylene glycol, macrogol, sodium monohydrogenphosphate, sodium dihydrogenphosphate, sodium phosphate, sodium chloride, phenol, salomethyl, sodium hydrogensulfite, etc. These are mixed with the compounds of the present invention to form various forms of pharmaceutical preparations.

The content of the active ingredient of the present invention in the anti-viral composition of the invention can greatly vary depending on the form of the pharmaceutical composition, and therefore is not specifically defined. In general, however, it may be from 0.01 to 100% by weight, preferably from 2 to 100% by weight, relative to the total weight of the composition.

Having generally described this invention, a further understanding can be obtained by reference to certain specific examples which are provided herein for purposes of illustration only and are not intended to be limiting unless otherwise specified.

EXAMPLES

EXAMPLE 1

Preparation of 1-[1'S,2'R-bis(hydroxymethyl)-cyclopropan-1'-yl]methyl-5-fluoro-2,4(1H,3H)pyrimidinedione:

Step 1: Preparation of ethyl(1S,5R)-3-oxa-2-oxobicyclo[3.1.0]hexane-1-carboxylate:

2.42 g (105 mmol) of metallic sodium were dissolved in 200 ml of ethanol at 0° C. under argon atmosphere. To this solution, added were 16.7 g (110 mmol) of diethyl malonate; and 7.8 ml (100 mmol) of R-(−)-epichlorohydrin dissolved in 5 ml of ethanol were dropwise added thereto at room temperature. The resulting solution was heated at 75° C. for 20 hours and then cooled to 0° C., and the precipitates thus formed were removed by filtration. The resulting filtrate was concentrated under reduced pressure, and water was added to the residue, which was then extracted with dichloromethane. The organic layer was dried with anhydrous sodium sulfate, and then the solvent was removed therefrom by distillation. The thus-obtained residue was subjected to silica gel chromatography (hexane:ethyl acetate=5:1 to 1:1) to obtain 12.0 g (70 mmol, 70%) of the entitled compound. This was colorless oil and had the following physical data:

$^1$H-NMR (CDCl$_3$) δ: 1.31 (t, J=7.1 Hz, 3H), 1.37 (dd, J=4.8, 5.4 Hz, 1H), 2.08 (dd, J=4.8, 8.0 Hz, 1H), 2.72 (m, 1H), 4.18 (d, J=9.6 Hz, 1H), 4.27 (q, J=7.1 Hz, 2H), 4.36 (dd, J=4.5, 9.6 Hz, 1H); FD mass: 170 (M$^+$)

Step 2: Preparation of ethyl (1S,2R)-1,2-bis(hydroxymethyl)-cyclopropanecarboxylate:

12.0 g (70 mmol) of ethyl (1S,5R)-3-oxa-2oxobicyclo[3.1.0]hexane-1-carboxylate were dissolved in 200 ml of ethanol, and 2.0 g (53 mmol) of sodium borohydride were added thereto. This solution was stirred for 2 hours at room temperature, and then 27 ml of 2N hydrochloric acid and 100 ml of ethyl acetate were added thereto. The precipitates thus formed were removed by filtration, and the filtrate was concentrated under reduced pressure. Water was added to the residue, which was the extracted with dichloromethane. The thus-obtained organic layer was dried with anhydrous sodium sulfate, and the solvent was removed therefrom by distillation. The thus-obtained oily residue was subjected to silica gel chromatography (dichloromethane:methanol=25:1) to obtain 8.35 g (48 mmol, 69%) of the entitled compound. This was colorless oil and had the following physical data:

$^1$H-NMR(CDCl$_3$) δ: 0.76 (dd, J=4.8, 6.6 Hz, 1H), 1.27 (t, J=7.2 Hz, 3H), 1.49 (dd, J=4.8, 9.0 Hz, 1H), 2.05 (m, 1H), 3.23 (d, J=12.8 Hz, 1H), 3.33 (dd, J=11.1, 12.5 Hz, 1H), 4.08 (dd, J=5.1, 12.5 Hz, 1H), 4.17 (q, J=7.2 Hz, 2H), 4.52 (d, J=12.8 Hz, 1H); FD mass 175 (MH$^+$)

Step 3: Preparation of ethyl (1R,7R)-4,4-diphenyl-3,5dioxabicyclo[5.1.0]octyl-1-carboxylate:

6.81 g (30 mmol) of 2,3-dichloro-5,6-dicyano-1,4benzoquinone were dissolved in 250 ml of 1,2-dichloroethane, and a solution prepared by dissolving 5.23 g (30 mmol) of ethyl (1S,2R)-1,2-bis(hydroxymethyl)cyclopropane-carboxylate obtained in the previous step 2 in Example 1 and 5.83 g (30 mmol) of diphenyldiazomethane in 130 ml of 1,2-dichloroethane was gradually and dropwise added thereto and thereafter stirred for one hour at room temperature. The resulting solution was concentrated under reduced pressure and then dissolved in toluene. The toluene solution was washed with a saturated aqueous solution of sodium hydrogencarbonate and dried with anhydrous sodium sulfate, and thereafter the solvent was removed therefrom by distillation under reduced pressure. The thus-obtained residue was subjected to silica gel chromatography (dichloromethane) to obtain 8.72 g (25.77 mmol, 85%) of the entitled compound. This was yellow oil and had the following physical data:

$^1$H-NMR(CDCl$_3$) δ: 1.22 (t, J=7.0 Hz, 3H), 1.33 (dd, J=3.6, 7.1 Hz, 1H), 1.43 (dd, J=3.6, 9.3 Hz, 1H), 1.8 (m, 1H), 3.68 (d, J=13.3 Hz, 1H), 3.76 (dd, J=3.1, 12.9 Hz, 1H), 4.1 (m, 3H), 4.65 (d, J=13.0 Hz, 1H), 7.2–7.6 (m, 10H); FD mass: 338 (M$^+$)

Step 4: Preparation of (1S,7R)-4,4-diphenyl-3,5-dioxabicyclo [5.1.0]octyl-1-methanol:

7.01 g (20.7 mmol) of ethyl (1R,7R)-4,4-diphenyl-3,5-dioxabicyclo[5.1.0]octyl-1 -carboxylate were dissolved in 10 ml of dry tetrahydrofuran, and 12 ml of 2 M lithium borohydride/tetrahydrofuran solution were added thereto and stirred for 16 hours at 72° C. under an argon atmosphere. After this was cooled to 0° C., a saturated aqueous solution of ammonium chloride was added thereto. Then, this was extracted with ethyl acetate. The organic layer was washed with water and dried with anhydrous sodium sulfate, and then the solvent was removed therefrom by distillation. The thus-obtained residue was subjected to silica gel chromatography (dichloromethane:methanol=19:1) to obtain 5.54 g (18.7 mmol. 90%) of the entitled compound. This was white solid, having a melting point of 93° C. and the following physical data:

$^1$H-NMR (CDCl$_3$) δ: 0.67 (dd, J=4.4, 8.9 Hz, 1H), 0.96 (dd, J=4.4, 5.8 Hz, 1H), 1.08 (m, 1H), 3.42 (dd, J=11.0, 27.9 Hz, 2H), 3.65 (dd, J=3.9, 12.9 Hz, 1H), 3.76 (d, J=12.7 Hz, 2H), 4.1 (m, 2H), 7.2–7.6 (m, 10H); FD mass: 296 (M$^+$)

Step 5: Preparation of (1R,7R)-1-bromomethyl-4,4-diphenyl-3,5-dioxabicyclo[5.1.0]octane:

5 g (16.87 mmol) of (1S,7R)-4,4-diphenyl-3,5-dioxabicyclo[5.1.0]octyl-1-methanol were dissolved in 100 ml of 1,2-dichloroethane, and 1.2 ml (8.4 mmol) of triethylamine, 7.97 g (30.4 mmol) of triphenylphosphine and 10.1 g (30.4 mmol) of carbon tetrachloride were added thereto and stirred for 20 minutes. To this, added was a saturated aqueous solution of sodium hydrogencarbonate, and the resulting mixture was extracted with hexane. The organic layer was washed with water and dried with anhydrous sodium sulfate, and then the solvent was removed therefrom by distillation under reduced pressure. The thus-obtained residue was subjected to silica gel chromatography (hexane:ethyl acetate=3:1) to obtain 5.45 g (15.1 mmol, 90%) of the entitled compound. This was yellow oil and had the following physical data:

$^1$H-NMR(CDCl$_3$) δ: 0.83 (dd, J=4.2, 8.5 Hz, 1H), 1.16–1.28 (m, 2H), 3.13 (d, J=10.2 Hz, 1H), 3.60 (dd, J=3.5, 12.9 Hz, 2H), 3.80 (d, J=12.9 Hz, 1H), 4.07 (dd, J=4.8, 13.0 Hz, 2H), 7.2–7.6 (m, 10H); FD mass: 358 (M$^+$)

Step 6: Preparation of 1-[1'S,2'R-bis(hydroxymethyl)-cycroplopan-1'-yl]methyl-5-fluoro-  2,4(1H,3H)-pyrimidinedione:

1.61 g (4.48 mmol) of (1R,7R)-1-bromomethyl-4,4-diphenyl-3,5-dioxabicyclo[5.1.0]octane was dissolved in 83 ml of dimethylformamide, and 700 mg (5.38 mmol) of 5-fluoro-2,4(1H,3H)-pyrimidinedione, 620 mg (4.49 mol) of potassium carbonate and 1.19 g (4.48 mol) of 18-crown-6 were added thereto. After stirring for 3 hours at 60° C., the mixture was cooled to room temperature and insoluble substances were removed therefrom by filtration. The filtrate was concentrated under reduced pressure, and 14 ml of methanol and 7 ml of 1N hydrochloric acid were added thereto. After the mixture was stirred for 25 minutes at room temperature, and methanol was removed therefrom by distillation under reduced pressure. This was adjusted to have pH 4, by adding potassium carbonate thereto, and subjected to reversed-phase C18 silica gel chromatography (water-:methanol=9:1) to obtain 177 mg (0.724 mmol, 16%) of the entitled compound. This was colorless solid and had the following physical data:

$^1$H-NMR (CD$_3$OD) δ: 0.56 (t, J=5.3 Hz, 1H), 0.99 (dd, J=5.3, 8.7 Hz, 1H), 1.37–1.47 (m, 1H), 3.46 (dd, J=9.3, 11.8 Hz, 1H), 3.52 (d, J=12.0 Hz, 1H), 3.78 (d, J=12.0 Hz, 1H), 3.80 (d, J=15.0 Hz, 1H), 3.84 (d, J=15.0 Hz, 1H), 3.87 (dd, J=6.2, 11.8 Hz, 1H), 7.89 (d, J=14.4, 1H)

High resolution mass spectrum (C$_{10}$H$_{14}$FN$_2$O$_4$, M+H): calculated value: 245.0938 measured value: 245.0941

EXAMPLE 2

Preparation of 1-[1'S,2'R-bis(hydroxymethyl)-cyclopropan-1'-yl]methyl-5-chloro-2,4(1 H,3H)-pyrimidinedione:

1.43 g (3.98 mmol) of (1R,7R)-1-bromomethyl-4,4-diphenyl3,5-dioxabicyclo[5.1.0]octane was dissolved in 77 ml of dimethylformamide, and 701 mg (4.78 mmol) of 5-chloro-2,4(1H,3H)-pyrimidinedione, 550 mg (3.98 mol) of potassium carbonate and 1.05 g (3.98 mol) of 18-crown-6 were added thereto. After stirring for 3.5 hours at 60° C., the mixture was cooled to room temperature and insoluble substances were removed therefrom by filtration. The filtrate was concentrated under reduced pressure, and 20 ml of methanol and 7.3 ml of 1N hydrochloric acid were added thereto. After the mixture was stirred for 1.5 hours at room temperature, and methanol was removed therefrom by distillation under reduced pressure. This was adjusted to have pH 4, by adding potassium carbonate, and subjected to reversed-phase C18 silica gel chromatography (water-:methanol=9:1) to obtain 322 mg (1.24 mmol, 31%) of the entitled compound. This was colorless solid and had the following physical data:

$^1$H-NMR (CD$_3$OD) δ: 0.56 (t, J=5.5 Hz, 1H), 1.00 (dd, J=5.5, 8.7 Hz, 1H), 1.38–1.48 (m, 1H), 3.46 (dd, J=9.3, 11.4 Hz, 1H), 3.52 (d, J=12.2 Hz, 1H), 3.78 (d, J=12.2 Hz, 1H), 3.85 (d, J=14.6 Hz, 1H), 3.87 (dd, J=6.9, 11.4 Hz, 1H), 3.87 (d, J=14.6 Hz, 1H), 8.02 (s, 1H)

High resolution mass spectrum (C$_{10}$H$_{14}$ClN$_2$O$_4$, M+H): calculated value: 261.0642 measured value: 261. 0638

EXAMPLE 3

Preparation of 1-[1'S,2'R-bis(hydroxymethyl)-cyclopropan-1'-yl]methyl-5-bromo-2,4(1 H,3H)-pyrimidinedione:

1.10 g (3.07 mmol) of (1R,7R)-1-bromomethyl-4,4-diphenyl-3,5-dioxabicyclo[5.1.0]octane was dissolved in 54 ml of dimethylformamide, and 702 mg (3.68 mmol) of 5-bromo-2,4(1H,3H)-pyrimidinedione, 422 mg (3.06 mol) of potassium carbonate and 809 mg (3.06 mol) of 18-crown-6 were added thereto. After stirring for 4 hours at 60° C., the mixture was cooled to room temperature and insoluble substances were removed therefrom by filtration. The filtrate was concentrated under reduced pressure, and 15.4 ml of methanol and 7.4 ml of 1N hydrochloric acid were added thereto. After the mixture was stirred for 35 minutes at room temperature, and methanol was removed therefrom by distillation under reduced pressure. This was adjusted to have pH 4, by adding potassium carbonate thereto, and subjected to reversed-phase C18 silica gel chromatography (water) to obtain 671 mg (2.20 mmol, 72%) of the entitled compound. This was colorless solid and had the following physical data:

$^1$H-NMR(CD$_3$OD) δ: 0.56 (t, J=5.3 Hz, 1H), 1.00 (dd, J=5.3, 9.0 Hz, 1H), 1.38–1.48 (m, 1H), 3.45 (dd, J=9.2, 11.8 Hz, 1H), 3.52 (d, J=12.2 Hz, 1H), 3.77 (d, J=12.2 Hz, 1H), 3.86 (s, 2H), 3.87 (dd, J=6.3, 11.8 Hz, 1H), 8.11 (s, 1H):

High resolution mass spectrum (C$_{10}$H$_{14}$BrN$_2$O$_4$, M+H): calculated value: 307.0117 measured value: 307. 0110

EXAMPLE 4

Preparation of 1-[1'S,2'R-bis(hydroxymethyl)-cyclopropan-1'-yl]methyl-5-iodo-2,4(1 H,3H)-pyrimidinedione:

3.77 g (10.5 mmol) of (1R,7R)-1-bromomethyl-4,4-diphenyl-3,5-dioxabicyclo[5.1.0]octane was dissolved in 123 ml of dimethylformamide, and 3.26 g (13.7 mmol) of 5-iodo-2,4(1H,3H)-pyrimidinedione, 1.46 g (10.6 mmol) of potassium carbonate and 2.76 g (10.4 mol) of 18-crown-6 were added thereto. After stirring for 14 hours at 60° C., the mixture was cooled to room temperature and insoluble substances were removed therefrom by filtration. The filtrate was concentrated under reduced pressure, and 37 ml of methanol and 37 ml of 1N hydrochloric acid were added thereto. After the mixture was stirred for 50 minutes at room temperature, and methanol was removed therefrom by distillation under reduced pressure. This was adjusted to have pH 4, by adding potassium carbonate thereto, and subjected to reversed-phase C18 silica gel chromatography (water-:methanol=8:2) to obtain 1.45 g (4.10 mmol, 72%) of the entitled compound. This was colorless solid and had the following physical data:

$^1$H-NMR (CD$^3$OD) δ: 0.55 (t, J=5.4 Hz, 1H), 1.00 (dd, J=5.4, 8.7 Hz, 1H), 1.36–1.47 (m, 1H), 3.45 (dd, J=9.0, 11.7 Hz, 1H), 3.51 (d, J=12.0 Hz, 1H), 3.76 (d, J=12.0 Hz, 1H), 3.86 (dd, J=6.3, 11.7 Hz, 1H), 3.86 (2H, s), 8.17 (s, 1H):

High resolution mass spectrum (C$_{10}$H$_{14}$IN$_2$O$_4$ M+H): calculated value: 352.9998 measured value:353.0007

EXAMPLE 5

Preparation of 1-[1'S,2'R-bis(hydroxymethyl)-cyclopropan-1'-yl]methyl-5-trifluoromethyl- 2,4(1H,3H)-pyrimidinedione:

830 mg (2.31 mmol) of (1R,7R)-1-bromomethyl-4,4-diphenyl-3,5-dioxabicyclo[5.1.0]octane was dissolved in 43.5 ml of dimethylformamide, and 500 mg (0.278 mmol) of 5-trifluoromethyl-2,4(1H,3 H)-pyrimidinedione, 320 mg (2.32 mol) of potassium carbonate and 611 mg (2.31 mol) of 18-crown-6 were added thereto. After stirring for 18.5 hours at 60° C., the mixture was cooled to room temperature and insoluble substances were removed therefrom by filtration. The filtrate was concentrated under reduced pressure, and 15 ml of methanol and 7 ml of 1N hydrochloric acid were added thereto. After the mixture was stirred for 25 minutes at room temperature, and methanol was removed therefrom by distillation under reduced pressure. This was adjusted to have pH 4, by adding potassium carbonate thereto, and subjected to reversed-phase C18 silica gel chromatography (water: methanol=9:1) to obtain 246 mg (0.835 mmol, 36%) of the entitled compound. This was colorless solid and had the following physical data:

$^1$H-NMR (CD$_3$OD) δ: 0.57 (t, J=5.3 Hz, 1H), 1.00 (dd, J=5.3, 8.9 Hz, 1H), 1.41–1.51 (m, 1H), 3.45 (dd, J=9.3, 12.0 Hz, 1H), 3.54 (d, J=12.3 Hz, 1H), 3.77 (d, J=12.3 Hz, 1H), 3.87 (d, J=14.4 Hz, 1H), 3.87 (dd, J=6.2, 12.0 Hz, 1H), 3.98 (d, J=14.4, 1H), 8.28 (q, J=1.1 Hz, 1H):

High resolution mass spectrum (C$_{11}$H$_{14}$F$_3$N$_2$O$_4$, M+H): calculated value: 295.0906 measured value: 295.0899

EXAMPLE 6

Preparation of 1-[1'S,2'R-bis(hydroxymethyl)cyclopropan-1'-yl]methyl-5-ethenyl-2,4(1 H,3H)-pyrimidinedione:

325 mg (0.905 mmol) of (1R,7R)-1-bromomethyl-4,4-diphenyl-3,5-dioxabicyclo[5.1.0]octane was dissolved in 17 ml of dimethylformamide, and 150 mg (1.09 mmol) of 5-ethenyl-2,4(1H,3H)-pyrimidinedione, 125 mg (0.905 mmol) of potassium carbonate and 239 mg (0.905 mmol) of 18-crown-6 were added thereto. After stirring for 18.5 hours at 60° C., the mixture was cooled to room temperature and insoluble substances were removed therefrom by filtration. The filtrate was concentrated under reduced pressure, and 8.5 ml of methanol and 4.0 ml of 1N hydrochloric acid were added thereto. After the mixture was stirred for 30 minutes at room temperature, and methanol was removed therefrom by distillation under reduced pressure. This was adjusted to have pH 4, by adding potassium carbonate thereto, and subjected to reversed-phase C18 silica gel chromatography (water:methanol=9:1) to obtain 99.8 mg (0.395 mmol, 44%) of the entitled compound. This was colorless solid and had the following physical data:

$^1$H-NMR (CD3OD) δ: 0.55 (t, J=5.4 Hz, 1H), 1.02 (dd, J=5.4, 8.6 Hz, 1H), 1.38–1.48 (m,1 H), 3.46 (dd, J=9.3, 12.1 Hz, 1H), 3.51 (d, J=12.2 Hz, 1H), 3.77 (d, J=12.2 Hz, 1H), 3.87 (dd, J=6.2, 12.1 Hz, 1H), 3.88 (s, 2H), 5.21 (d, J=11.3 Hz, 1H), 5.99 (d, 17.8 Hz, 1H), 6.47 (dd, J=11.3, 17.8 Hz, 1H), 7.81 (s, 1H):

High resolution mass spectrum (C$_{12}$H$_{17}$N$_2$O$_4$, M+H): calculated value: 253.1188 measured value:235.1184

EXAMPLE 7

Preparation of 1-[1'S, 2'R-bis(hydroxymethyl)-cyclopropan-1'-yl]methyl-5-[(E)-2 -chloroethenyl]-2,4(1H,3H)-pyrimidinedione:

311 mg (0.866 mmol) of (1R,7R)-1-bromomethyl-4,4-diphenyl-3,5-dioxabicyclo[5.1.0]octane was dissolved in 14.6 ml of dimethylformamide, and 150 mg (0.869 mmol) of 5-[(E)-2-chloroethenyl]-2,4(1H,3 H)-pyrimidinedione, 120 mg (0.868 mmol) of potassium carbonate and 191 mg (0.723 mmol) of 18-crown-6 were added thereto. After stirring for 1.5 hours at 60° C., the mixture was cooled to room temperature and insoluble substances were removed therefrom by filtration. The filtrate was concentrated under reduced pressure, and 7 ml of methanol and 3.3 ml of 1N hydrochloric acid were added thereto. After the mixture was stirred for 20 minutes at room temperature, and methanol was removed therefrom by distillation under reduced pressure. This was adjusted to have pH 4, by adding potassium carbonate thereto, and subjected to reversed-phase C18 silica gel chromatography (water:methanol=8:2) to obtain 108 mg (0.378 mmol, 51%) of the entitled compound. This was colorless solid and had the following physical data:

$^1$H-NMR (CD$_3$OD) δ: 0.56 (t, J=5.4 Hz, 1H), 1.01 (dd, J=5.4, 8.7 Hz, 1H), 1.38–1.49 (m, 1H), 3.45 (dd, J=9.3, 12.2 Hz, 1H), 3.51 (d, J=12.3 Hz, 1H), 3.76 (d, J=12.3 Hz, 1H), 3.81 (d, J=14.4 Hz, _H), 3.88 (dd, J=5.9, 12.2 Hz, 1H), 3.92 (d, J=14.4 Hz, 1H), 6.56 (d, J=13.4 Hz, 1H), 7.26 (d, J=13.4 Hz, 1H), 7.78 (s,1H):

High resolution mass spectrum (C$_{12}$H$_{16}$ClN$_2$O$_4$, M+H): calculated value:287.0799 measured value:287.0812

EXAMPLE 8

Preparation of 1-[1'S,2'R-bis(hydroxymethyl)-cyclopropan-1'-yl]methyl-5-[(E)-2 -bromoethenyl]-2,4(1H,3H)-pyrimidinedione:

71.1 mg (198 μmol) of (1R,2R)-1-bromomethyl-4,4-diphenyl-3,5-dioxabicyclo[5.1.0 ]octane was dissolved in 4 ml of dimethyformamide, and 42.9 mg (198 μmol) of 5-[(E)-2-bromoethenyl]-2,4(1H,3 H)-pyrimidinedione, 27.4 mg (198 μmol) of potassium carbonate and 52.3 mg (198 μmol) of 18- crown-6 were added thereto. After stirring for 2 hours at 60° C., the mixture was cooled to room temperature and insoluble substances were removed therefrom by filtration. The filtrate was concentrated under reduced pressure, and 2 ml of methanol and 0.5 ml of 2N hydrochloric acid were added thereto. After the mixture was stirred for 30 minutes at room temperature, and methanol was removed therefrom by distillation under reduced pressure. This was adjusted to have pH 4, by adding potassium carbonate thereto, and subjected to reversed-phase C18 silica gel chromatography (water:methanol=7:3) to obtain 13.0 mg (39.3 μmol, 20%) of the entitled compound. This was colorless solid and had the following physical data:

$^1$H-NMR(DMSO-d$_6$) δ: 0.42 (t, J=5.4 Hz, 1H), 0.80 (dd, J=4.8, 8.7 Hz, 1H), 1.20–1.30 (m, 1H), 3.24–3.37 (m, 2H), 3.50 (dd, J=6.0, 12.0 Hz, 1H), 3.61 (dt, J=12.0, 6.0 Hz, 1H), 3.61 (d, J=14.1 Hz, 1H), 3.77 (d, J=14.1 Hz, 1H), 4.50–4.59 (m, 2H), 6.81 (d, J=13.5 Hz, 1H), 7.23 (d, J=13.5 Hz, 1H), 7.91 (s, 1H):

High resolution mass spectrum (C$_{12}$H$_{16}$BrN$_2$O$_4$, M+H): calculated value:331.0293 measured value:331.0298

EXAMPLE 9

Preparation of 1-[1'S,2'R-bis(hydroxymethyl)-cyclopropan-1'-yl]methyl-5-[(E)-2 -bromoethenyl]-2,4(1H,3H)-pyrimidinedione:

Step 1: Preparation of 1-[1'S,2'R-bis(hydroxymethyl)-cyclopropan-1'-yl]methyl- 2,4(1H,3H)-pyrimidinedione:

973 mg (2.26 mmol) of (1R,7R)-1-bromomethyl-4,4-diphenyl3,5-dioxabicyclo[5,1,0]octane were dissolved in 5 ml of dimethylsulfoxide, and 304 mg (2.71 mmol) of uracil, 375 mg (2.71 mmol) of potassium carbonate and 597 mg (2.26 mmol) of 18-crown-6 were added thereto. After stirred for 5 days at 100° C., the mixture was cooled to room temperature and the insoluble substances were removed therefrom by filtration. The filtrate was concentrated under reduced pressure, and 2 ml of methanol and 0.5 ml of 2N hydrochloric acid were added thereto. After this was stirred for 30 minutes at room temperature, the methanol was removed therefrom by distillation under reduced pressure. This was adjusted to have pH 4, by adding potassium carbonate thereto, and purified by reversed-phase C18 silica gel chromatography (water:methanol=8:2) to obtain 113 mg (0.497 mmol, 22%) of the entitled compound. This was white solid and had the following physical data:

$^1$H-NMR(CDCl$_3$) δ: 0.55 (t, J=5.4 Hz, 1H), 1.00 (dd, J=5.4, 9.0 Hz, 1H), 1.35–1.46 (m, 1H), 3.46(dd, J=9.3, 12.0 Hz, 1H), 3.49 (d, J=12.3 Hz, 1H), 3.77 (d, J=12.3HZ, 1H), 3.83–3.92 (m, 3H), 5.68 (d, J=7.8 Hz, 1H), 7.69 (d, J=7.8 Hz, 1H)

High resolution mass spectrum (C$_{10}$H$_{15}$N2O$_4$, M+H): calculated value: 227.1032 measured value: 227.1008

Step 2: Preparation of 1-[1'S,2'R-bis(hydroxymethyl)-cyclopropan-1'-yl]methyl-5 -iodo-2,4(1H,3H)-pyrimidinedione:

45.0 mg (0.199 mmol) of 1-[1'S,2'R-bis(hydroxymethyl)-cyclopropan-1'-yl]methyl-2,4 (1H,3H) pyrimidinedione were dissolved in 4 ml of dioxane, and 102 mg (0.40 mmol) of iodine and 0.267 ml of 0.8N nitric acid were added thereto. After stirred for 4 hours at 95° C., this was cooled to room temperature, and a saturated aqueous solution of sodium thiosulfate was added thereto until the color of the reaction liquid disappeared. The solvent was removed by distillation under reduced pressure, and the residue was subjected to silica gel chromatography (dichloromethane:methanol=19:1) to obtain 33.5 mg (95.5 μmol, 48%) of the entitled compound. This was white solid and had the following physical data:

$^1$H-NMR (CDCl$_3$) δ: 0.55 (t, J=5.4 Hz, 1H), 1.00 (dd, J=5.4, 8.7 Hz, 1H), 1.36–1.47 (m, 1H), 3.45 (dd, J=9.0, 11.7 Hz, 1H), 3.51 (d, J=12.0 Hz, 1H), 3.76 (d, J=12.0 Hz, 1H), 3.86 (dd, J=6.3, 11.7 Hz, 1H), 3.86 (s, 2H), 8.17 (s, 1H)

High resolution mass spectrum (C$_{10}$H$_{14}$IN$_2$O$_4$, M+H): calculated value: 352.9998 measured value: 353.0007

Step 3: Preparation of 1-[1'S,2'R-bis(hydroxymethyl)cyclopropan-1'-yl]methyl-5-[(E)- 2-methoxycarbonylethenyl]-2,4(1H,3H)-pyrimidinedione:

Dry dioxane (6.7 ml, purified by passage through basic alumina) was deoxygenated. To the deoxygenated dioxane were added 45.1 mg (0.201 mmol) of palladium (II) acetate, 104.6 mg (0.399 mmol) of triphenylphosphine, and 556 mg (5.49 mmol) of triethylamine. The mixture was stirred for 40 minutes at 70° C. Then 704 mg (200 mmol) of 1-[1'S,2'R-bis-(hydroxymethyl)-cyclopropan-1'-yl]methyl-5-iodo-2,4(1H,3H)-pyrimidinedione and methyl acrylate (3.56 mg, 4.13 mmol) were added thereto, and the mixture was stirred for 3 hours at 70° C. The reaction mixture was filtered, and the filtrate was concentrated under reduced pressure. The mixture was subjected to silica gel chromatography (dichloromethane: methanol=19:1) to obtain 458 mg (1.48 mmol, 74%) of the entitled compound. This was yellow solid and had the following data:

$^1$H-NMR (CD$_3$OD) δ: 0.57 (t, J=5.4 Hz, 1H), 1.02 (dd, J=5.4, 8.7 Hz, 1H), 1.41–1.51 (m, 1H), 3.45 (dd, J=9.5, 11.8 Hz, 1H), 3.53 (d, J=12.3 Hz, 1H), 3.78 (d, J=12.3 Hz, 1H), 3.78 (s, 3H), 3.81 (d, J=14.2 Hz, 1H), 3.88 (dd, J=6.3, 11.8 Hz, 1H), 4.01 (d, J=14.2 Hz, 1H), 6.96 (d, J=15.6 Hz, 1H), 7.45 (d, J=15.6 Hz, 1H), 8.12 (s,1H)

FAB MASS: 311 (MH+)

Step 4: Preparation of 1-[1'S,2'R-bis(hydroxymethyl)-cyclopropan -1'-yl]methyl-5-[ (E)-2-carboxyethenyl]-2,4(1H, 3H)-pyrimidinedione:

216 mg (0.694 mmol) of 1-[1'S,2'R-bis(hydroxymethyl)-cyclopropan-1'-yl]methyl-S-[(E)- 2-methoxycarbonylethenyl]-2,4(1H,3H)-pyrimidinedione was dissolved in 1.5 ml of 2N sodium hydroxide solution. The solution was stirred at room temperature for 45 minutes and then filtered. The filtrate was cooled to 0° C., and stirred for 30 minutes, and was adjusted to have pH 2.0 by adding 6N hydrochloric acid. The precipitate was filtrated, and washed with cold water, air-dried, and then dried overnight in vacuo at room temperature to obtain 141 mg (0.477 mmol, 69%) of the entitled compound. This was white solid and had the following physical data:

$^1$H-NMR(CD$_3$OD) δ: 0.41 (t, J=5.1 Hz, 1H), 0.82 (dd, J=5.0, 8.6 Hz, 1H), 1.23 –1.33 (m, 1H), 3.46 –3.61 (m, 4H), 3.65 (d, J=14.1 Hz, 1H), 3.82 (d, J=14.1 Hz, 1H), 4.57 (2H, bs), 6.76 (d, J=15.8 Hz, 1H), 7.27 (d, J=15.8 Hz, 1H), 8.19 (s, 1H), 11.5 (bs, 1H)

FAB MASS: 297 (MH+)

Step 5: Preparation of 1-[1'S,2'R-bis(hydroxymethyl)-cyclopropan-1'-yl]methyl-5-[ (E)-2-bromoethenyl]-2,4(1H, 3H)-pyrimidinedione:

10.0 mg (0.034 mmol) of 1-[1'S,2'R-bis(hydroxymethyl)-cyclopropan-1'-yl]methyl-5-[ (E)-2-carboxyethenyl]-2,4(1H,3H)-pyrimidinedione were dissolved in 183 μl of dry dimethylformamide, and 10.3 mg (0.102 mmol) of potassium hydrogen carbonate and 6.8 mg (0.038 mmol) N-bromosuccinimide thereto. After stirred for 2.5 hours at room temperature, the mixture was filtered, and the filtrate was concentrated under reduced pressure. The mixture was subjected to reversed-phase C18 silica gel chromatography (water:methanol=9:1) to obtain 8.4 mg (0.025 mmol, 75%) of the entitled compound. The 1H-NMR spectrum and FAB MASS spectrum of this compound were completely identical to those of the compound prepared in Example 8.

EXAMPLE 10

Preparation of 1-[1'S,2'R-bis(hydroxymethyl)-cyclopropan-1'-yl]methyl-5-[(E)-2 -iodoethenyl]-2,4(1H,3H)-pyrimidinedione:

61 mg (0.171 mmol) of (1R,7R)-1-bromomethyl-4,4-diphenyl3,5-dioxabicyclo[5.1.0]octane were dissolved in 3.9 ml of dimethylformamide, and 45 mg (0.170 mmol) of 5-[(E)-2-iodoethenyl]-2,4(1H,3 H)-pyrimidinedione, 24 mg (0.174 mmol) of potassium carbonate and 38 mg (0.144 mmol) of 18-crown-6 were added thereto. After stirring for 1.5 hours at 60° C., the mixture was cooled to room temperature and insoluble substances were removed therefrom by filtration. The filtrate was concentrated under reduced pressure, and 0.52 ml of methanol and 1.0 ml of 1N hydrochloric acid were added thereto. After the mixture was stirred for 20 minutes at room temperature, and methanol was removed therefrom by distillation under reduced pressure. This was adjusted to have pH 4 by adding potassium carbonate thereto, and subjected to reversed-phase C18 silica gel chromatography (water:methanol=7:3) to obtain 11.2 mg (29.6 μmol, 26%) of the entitled compound. This was colorless solid and the following physical data:

$^1$H-NMR (CD$_3$OD) δ: 0.56 (t, J=5.4 Hz, 1H), 1.00 (dd, J=5.4, 8.7 Hz, 1H), 1.38–1.48 (m, 1H), 3.45 (dd, J=9.6, 12.3 Hz, 1H), 3.51 (d, J=12.3 Hz, 1H), 3.76 (d, J=12.3 Hz, 1H), 3.81 (d, J=14.6 Hz), 3.88 (dd, J=5.6, 12.3 Hz, 1H), 3.92 (d, J=14.6 Hz, 1H), 7.16 (d, J=14.7 Hz, d), 7.34 (d. J=14.7 Hz, 1H), 7.80 (s, 1H):

High resolution mass spectrum (C$_{12}$H$_{16}$IN$_2$O$_4$, M+H): calculated value: 379. 0155 measured value: 379.0156

EXAMPLE 11

Preparation of 1-[1'S,2'R-bis(hydroxymethyl)-cyclopropan-1'-yl]methyl-5-ethynyl-2,4( 1H,3H)-pyrimidinedione:

165 mg (0.460 mmol) of (1R,7R)-1-bromomethyl-4,4-diphenyl3,5-dioxabicyclo[5.1.0]octane was dissolved in 8.7 ml of dimethylformamide, and 75 mg (0.55 mmol) of 5-ethynyl-2,4(1H,3H)-pyrimidinedione, 63.5 mg (0.460 mmol) of potassium carbonate and 122 mg (0.460 mmol) of 18-crown-6 were added thereto. After stirring for 18.5 hours at 60° C., the mixture was cooled to room temperature and insoluble substances were removed therefrom by filtration. The filtrate was concentrated under reduced pressure, and 3.7 ml of methanol and 1.8 ml of 1N hydrochloric acid were added thereto. After the mixture was stirred for 20 minutes at room temperature, and methanol was removed therefrom by distillation under reduced pressure. This was adjusted to have pH 4 by adding potassium carbonate, and the mixture was subjected to reversed-phase C18 silica gel chromatography (water:methanol=9:1) to obtain 22.6 mg (0.106 mmol, 23%) of the entitled compound. This was colorless solid and have the following physical data:

$^1$H-NMR (CD$_3$)D) δ: 0.56 (t, J=5.6 Hz, 1H), 1.01 (dd, J=5.6, 8.7 Hz, 1H), 1.38–1.48 (m, 1H), 3.46 (dd, J=9.2, 12.3 Hz, 1H), 3.51 (d, J=12.3 Hz, 1H), 3.59 (s, 1H), 3.77 (d, J=12.3 Hz, 1H), 3.86 (dd, J=5.7, 12.3 Hz, 1H), 3.87 (s, 2H), 8.05 (s, 1H):

High resolution mass spectrum (C$_{12}$H$_{15}$N$_2$O$_4$, M+H): calculated value: 251.1032 measured value: 251.1027

EXAMPLE 12

Preparation of 1-[1'S,2'R-bis(hydroxymethyl)-cyclopropan-1'-yl]methyl-5-(1-propynyl)- 2,4(1H,3H)-pyrimidinedione:

70 mg (0.195 mmol) of (1R,7R) -1-bromomethyl-4,4-diphenyl-3,5-dioxabicyclo[5.1.0]octane was dissolved in 7 ml of dimethylformamide, and 35 mg (0.233 mmol) of 5-(1-propynyl)2,4(1H,3H)-pyrimidinedione, 28.5 mg (0.206 mmol) of potassium carbonate and 53 mg (0.201 mmol) of 18-crown-6 were added thereto. After stirring for 3 hours at 60° C., the mixture was cooled to room temperature and insoluble substances were removed therefrom by filtration. The filtrate was concentrated under reduced pressure, and 5 ml of methanol and 0.8 ml of 1N hydrochloric acid were added thereto. After the mixture was stirred for 40 minutes at room temperature, and methanol was removed therefrom by distillation under reduced pressure. This was adjusted to have pH 4 by adding potassium carbonate, and the mixture was subjected to reversed-phase C18 silica gel chromatography (water:methanol=9:1) to obtain 33.4 mg (0.126 mmol, 61%) of the entitled compound. This was colorless solid and had the following physical data:

$^1$H-NMR (CD$_3$OD) δ: 0.55 (t, J=5.4 Hz, 1H), 1.00 (dd, J=5.4, 8.6 Hz, 1H), 1.36–1.46 (m, 1H), 2.03 (s, 3H), 3.46 (dd, J=9.3, 12.0 Hz, 1H), 3.50 (d, J=12.3 Hz, 1H), 3.76 (d, J=12.3 Hz, 1H), 3.80 (d, J=14.3 Hz, 1H), 3.86 (dd, J=6.2, 12.0 Hz, 1H), 3.90 (d, J=14.3 Hz, 1H), 7.87 (s, 1H)

High resolution mass spectrum (C$_{13}$H$_{17}$N$_2$O$_4$, M+H): calculated value: 265.1188 measured value: 265.1190

EXAMPLE 13

Preparation of 1-[1'S,2'R-bis(hydroxymethyl)-cyclopropan-1'-yl]methyl-5-ethyl-2,4(1 H,3H)-pyrimidinedione:

29.8 mg (0.090 mmol) of 1-[1'S,2'R-bis(hydroxymethyl)-cyclopropan-1'-yl]methyl-5-[ (E)-2-bromoethenyl]- -2,4 (1H,3H)-pyrimidinedione was dissolved in 0.9 ml of methanol, 2.77 mg of palladium carbon (10%) was added thereto, and the mixture was stirred in hydrogens atmosphere for 10 hours. The mixture was filtered, and the filtrate was concentrated under reduced pressure, and subjected to reversed-phase C18 silica-gel chromatography (water:methanol=9:1) to obtain 22.9 mg (0.090 mmol, 100%) of the entitled compound. This was colorless solid and had the following physical data:

$^1$H-NMR (CD$_3$OD) δ: 0.54 (t, J=5.4 Hz, 1H), 1.00 (dd, J=5.4, 8.9 Hz, 1H), 1.17 (t, J=7.5 Hz, 3H), 1.36–1.46 (m, 1H), 2.37 (dq, J=1.1, 7.5 Hz, 2H), 3.46 (dd, J=9.2, 11.7 Hz, 1H), 3.49 (d, J=12.0 Hz, 1H), 3.77 (d, J=12.0 Hz, 1H), 3.84 (s, 2H), 3.87 (dd, J=6.0, 11.7 Hz, 1H), 7.51 (t, J=1.1 Hz, 1H)

High resolution mass spectrum (C$_{12}$H$_{19}$N$_2$O$_4$, M+H): calculated value: 255.1345 measured value: 255.1359

EXAMPLE 14

Preparation of 1-[1'R,2'S-bis(hydroxymethyl)-cyclopropan-1'-yl]methyl-5-[(E)-2 -bromoethenyl]-2,4(1H,3H)-pyrimidinedione:

261 mg (0.561 mmol) of (1'R,2'S)bis(benzoyloxymethyl)-cyclopropan-1'-yl]methyl p-toluenesulfonate was dissolved in 5 ml of dimethylformamide, and 121.7 mg (0.561 mmol) of 5-[(E)-2-bromoethenyl]-2,4(1H,3H)pyrimidinedione, 78 mg (0.561 mmol) of potassium carbonate and 149 mg (0.561 mmol) of 18-crown-6 were added thereto. After stirring for 15 hours at 60° C., the mixture was cooled to room temperature and insoluble substances were removed therefrom by filtration. The filtrate was concentrated under reduced pressure, and 5.0 ml of sodium methoxide, 0.1 M solution in methanol was added thereto. After the mixture was stirred for 14 hours at room temperature, pH was adjusted to 3 by adding 2N hydrochloric acid, and methanol was removed therefrom by distillation under reduced pressure. The mixture was subjected to reversed-phase C18 silica gel chromatography (water: methanol=2:1) to obtain 25.6 mg (0.077 mmol, 14%) of the entitled compound. This was colorless solid and had the following physical data:

$^1$H-NMR(DMSO-d$_6$) δ: 0.42 (t, J=5.4 Hz, 1H), 0.80 (dd, J=4.8, 8.7 Hz, 1H), 1.20–1.30 (m, 1H), 3.24–3.37 (m, 2H), 3.50 (dd, J=6.0, 12.0 Hz, 1H), 3.61 (dt, J=12.0, 6.0 Hz, 1H), 3.61 (d, J=14.1 Hz, 1H), 3.77 (d, J=14.1 Hz, 1H), 4.50–4.59 (m, 2H), 6.81 (d, J=13.5 Hz, 1H), 7.23 (d, J=13.5 Hz, 1H), 7.91 (s, 1H)

High resolution mass spectrum (C$_{12}$H16$_{16}$BrN$_2$O$_4$, M+H) calculated value: 331.0293 measured value: 331.0295

EXAMPLE 15

Preparation of 1-[1'α,2'β-2-bis(hydroxymethyl) cyclopropanyl-yl]methyl-5-[(E)-2-bromoethenyl]-2,4(1H,3H)-pyrimidinedione:

475 mg (0.960 mmol) of (1'α,2'β)-bis(benzoyloxymethyl)-cyclopropan-1'-yl]methyl p-toluenesulfonate was dissolved in 19 ml of dimethylformamide, and 250 mg (1.15 mmol) of 5-[(E)-2-bromoethenyl]-2,4(1H,3H)-pyrimidinedione, 159 mg (1.15 mmol) of potassium carbonate and 277 mg (1.15 mmol) of 18-crown-6 were added thereto. After stirring for 12 hours at 60° C., the mixture was cooled to room temperature and insoluble substances were removed therefrom by filtration. The filtrate was concentrated under reduced pressure, and 89.8 μl of sodium methoxide, 28% solution in methanol and 0.9 ml of methanol were added thereto. After the mixture was stirred for 30 minutes at room temperature, 0.44 ml of 1N hydrochloric acid was added, and methanol was removed therefrom by distillation under reduced pressure. The mixture was subjected to silica gel chromatography (dichloromethane:methanol=13:1) to obtain 27.0 mg (0.082 mmol, 9%) of the entitled compound. This was colorless solid and had the following physical data:

$^1$H-NMR (DMSO-d$_6$) δ: 0.50 (t, J=5.1 Hz, 1H), 0. 58 (dd, J=5.1, 8.8 Hz, 1H), 1.05–1.15 (m, 1H), 3.11–3.37 (m, 3H), 3.65–3.75 (m, 1H), 3.85 (d, J=14.6 Hz, 1H), 3.92 (d, J=14.6 Hz, 1H), 4.55 (t, J=5.4 Hz, 1H), 4.65 (t, J=5.4 Hz, 1H), 6.80 (d, J=13.7 Hz, 1H), 7.22 (d, J=13.7 Hz, 1H), 7.99 (s, 1H), 11.48 (bs, 1H)

High resolution mass spectrum (C$_{12}$H$_{16}$BrN$_2$O$_4$, M+H): calculated value: 331.0293 measured value: 331.0313

EXAMPLE 16

Anti-viral activity against herpes simplex virus:

The anti-viral activity of the prepared compounds against herpes simplex virus was measured by neutral red dye-uptake method (J. Infect. Dis. 148: 868 (1983)) with modification. Precisely, threefold dilutions of the compounds were prepared in 100 μl volumes of culture medium in the wells of a 96-well culture plate. Sixty microliters of a suspension of Vero cells ($3 \times 10^5$ cells/ml) were then dispensed into each well. HSV-1 (Tomioka strain) was diluted in medium to approximately 100 $TCID_{50}/40$ µl, as determined by prior titration in a similar dye uptake assay, and 40 µl of viral suspension were added to the respective wells. Control wells containing no test compound and no virus (cell control) or no cells (blank control) were included in each plate. After 3 days incubation at 37° C. in 5% $CO_2$ atmosphere, 50 µl of neutral red dye (0.15% in saline, pH 5.5) was dispensed into each well and the cultures were incubated for a further 45 min at 37° C. Unincorporated dye was removed by rinsing with PBS. The dye incorporated by viable cells was then eluted into 100 µl per well of citrate ethanol buffer (pH 4.2; equal volumes of 0.1 M Sorensen citrate buffer and ethanol), and absorbance at 540 nm of the solution was measured. The absorbance of cell control was assigned 100% and that of blank control was assigned 0%, and the 50% absorbance concentration ($ID_{50}$) of the test compound was determined. The $ID_{50}$ value of each compound is shown in Table 1. As a comparative compound, acyclovir was used.

TABLE 1

| Test compound | $ID_{50}$ (µg/ml) | Cytotoxicity ($CD_{50}$ (µg/ml)) |
| --- | --- | --- |
| Example 1 | >500 | >500 |
| Example 2 | 295 | >500 |
| Example 3 | 215 | >500 |
| Example 4 | 90 | >500 |
| Example 5 | >500 | 234 |
| Example 6 | 3.20 | >500 |
| Example 7 | 4.30 | >500 |
| Example 8 | 14.5 | >500 |
| Example 10 | 24.6 | 330 |
| Example 11 | 310 | >500 |
| Example 12 | 325 | >500 |
| Example 13 | 24.3 | >500 |
| Example 14 | >500 | >500 |
| Example 15 | 78.0 | >500 |
| acyclovir | 0.80 | >500 |

EXAMPLE 17

Anti-viral activity against varicella zoster virus:

The activity of test compounds against varicella zoster virus was measured by plaque reduction assay. Confluent monolayers of human embryonic lung (HEL) cells grown in 6-well plates were infected with varicella zoster virus (Kawaguchi strain) in such a way that each well might have 100 plaque-forming units. After incubated at 37 C. for one hour in 5% CO2 atmosphere, the inoculum was removed and 3 ml of maintenance media containing the test compound having a varying concentration was added thereto. The incubation was continued for 3 days. After incubation, the cells were fixed and stained, the number of plaques was counted microscopically. In comparison to the control, the 50% plaque decrease concentration ($PI_{50}$) of the test compound was determined. The $PI_{50}$ value of each compound was shown in Table 2. As a comparative compound, acyclovir was used.

TABLE 2

| Test compound | $PI_{50}$ (µg/ml) |
| --- | --- |
| Example 1 | >100 |
| Example 2 | >100 |
| Example 3 | 97 |
| Example 4 | 9.3 |

TABLE 2-continued

| Test compound | $PI_{50}$ (µg/ml) |
| --- | --- |
| Example 5 | >100 |
| Example 6 | 11.1 |
| Example 7 | 0.07 |
| Example 8 | 0.031 |
| Example 10 | 0.054 |
| Example 11 | >100 |
| Example 12 | 19.8 |
| Example 13 | 95 |
| Example 14 | 7.4 |
| Example 15 | 87 |
| acyclovir | 4.1 |

18

Preparation of a formulation for injection and eye drops:

One g of 1-[1'S,2'R-bis(hydroxymethyl)cyclopropan-1'-yl]methyl-5-[(E)-2-bromoethenyl] -2,4(1H,3H)-pyrimidinedione was dissolved in 600 ml of distilled water, and filtered by a Millipore filter for sterilization. 15 g of the filtrate were put in a 20 ml-vial and lyophilized to obtain a freeze-dried preparation containing 25 mg/vial of the compound.

EXAMPLE 19

Preparation of a formulation of tablets:

10 g of 1-[1'S,2'R-bis(hydroxymethyl)cyclopropan-1'-yl1-methyl-5-[(E)-2 -bromoethenyl]-2,4(1H,3H)-pyrimidinedione, 40 g of lactose, 49 g of crystalline cellulose and 1 g of magnesium stearate were well mixed and formed into tablets, using a tabletting machine. The tablets contained 250 mg/tablet of the active ingredient.

EXAMPLE 20

Preparation of a formulation of granules:

10 g of 1-[1'S,2'R-bis(hydroxymethyl)cyclopropan-1'-yl] methyl-5-[(E)-2 -bromoethenyl]-2,4(1H,3H)-pyrimidinedione, 90 g of lactose and 100 g of crystalline cellulose were well mixed, compressed, using a roll compressor, powdered and sieved to obtain granules of 20 to 80-mesh.

The compounds of the present invention have an excellent anti-vital activity against varicella-zoster viruses and herpes simplex viruses and are expected to be useful as anti-viral agents.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A cyclopropane derivative of the formula (I):

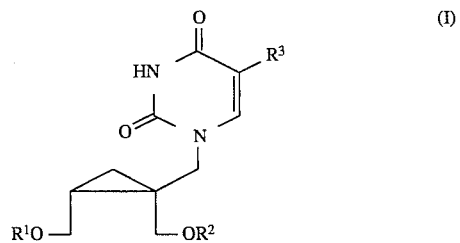

wherein $R^1$ and $R^2$, the same or different, are each a hydrogen atom, a $C_{1-6}$ acyl group or a $C_{1-6}$ acyl group substituted with a $C_{3-8}$ cycloalkyl group or $C_{6-8}$ aryl group; $R^3$ is an (E)-2-haloethenyl group;

or a pharmaceutically acceptable salt thereof.

2. The cyclopropane derivative of claim 1, wherein said $C_{1-6}$ acyl group is selected from the group consisting of formyl, acetyl, propionyl, butyryl, valeryl, isovaleryl, pivalyl and hexanoyl.

3. The cyclopropane derivative of claim 1, wherein said $C_{1-6}$ acyl group substituted with a $C_{3-8}$ cycloalkyl group is a cyclohexanecarbonyl group.

4. The cyclopropane derivative of claim 1, wherein said $C_{1-6}$ acyl group substituted with a $C_{6-8}$ aryl group is a benzoyl group.

5. The cyclopropane derivative of claim 1 which is selected from the group consisting of:

1-[1'α,2'α-bis(hydroxymethyl)-cyclopropan-1'β-yl]methyl-5-[(E)-2-bromoethenyl]- 2,4(1H,3H)-pyridinedione;

1-[1'α,2'β-bis(hydroxymethyl)-cyclopropan-1'β-yl]methyl-5-[(E)-2-bromoethenyl]- 2,4(1H,3H)-pyridinedione;

1-[1'α,2'α-bis(hydroxymethyl)-cyclopropan-1'β-yl]methyl-5-[(E)-2-chloroethenyl]- 2,4(1H,3H)-pyridinedione;

1-[1'α,2'β-bis(hydroxymethyl)-cyclopropan-1'β-yl]methyl-5-[(E)-2-chloroethenyl]- 2,4(1H,3H)-pyridinedione;

1-[1'α,2'α-bis(hydroxymethyl)-cyclopropan-1'β-yl]methyl-5-[(E)-2-iodoethenyl]- 2,4(1H,3H)-pyridinedione;

1-[1'α,2'β-bis(hydroxymethyl)-cyclopropan-1'β-yl]methyl-5-[(E)-2-iodoethenyl]- 2,4(1H,3H)-pyridinedione;

1-[1'α,2'α-bis(acetoxymethyl)-cyclopropan-1'β-yl]methyl-5-[(E)-2-bromoethenyl]- 2,4(1H,3H)-pyridinedione;

1-[1'α,2'β-bis(acetoxymethyl)-cyclopropan-1'β-yl]methyl-5-[(E)-2-bromoethenyl]- 2,4(1H,3H)-pyridinedione;

1-[1'α,2'α-bis(acetoxymethyl)-cyclopropan-1'β-yl]methyl-5-[(E)-2-chloroethenyl]- 2,4(1H,3H)-pyridinedione;

1-[1'α,2'β-bis(acetoxymethyl)-cyclopropan-1'β-yl]methyl-5-[(E)-2-chloroethenyl]- 2,4(1H,3H-pyridinedione;

1-[1'α,2'α-bis(acetoxymethyl)-cyclopropan-1'β-yl]methyl-5-[(E)-2-iodoethenyl]- 2,4(1H,3H)-pyridinedione;

1-[1'α,2'β-bis(acetoxymethyl)-cyclopropan-1'β-yl]methyl-5-[(E)-2-iodoethenyl]- 2,4(1H,3H)-pyridinedione.

6. The compound of claim 1, which is 1-[1'S,2'R-bis(hydroxymethyl)-cyclopropan-1'-yl]methyl-5 -[(E)-2-chloroethenyl]-2,4(1H,3)-pyridinedione.

7. The compound of claim 1, which is 1-[1'S,2'R-bis(hydroxymethyl)-cyclopropan-1'-yl]methyl-5 -[(E)-2-bromoethenyl]-2,4(1H,3H)-pyridinedione.

8. The compound of claim 1, which is 1-[1'S,2'R-bis(hydroxymethyl)-cyclopropan-1'-yl]methyl-5 -[(E)-2-iodoethenyl]-2,4(1H,3H)-pyridinedione.

9. A pharmaceutical composition comprising an anti varicella zoster viral effective amount of a cyclopropane derivative of the formula (I):

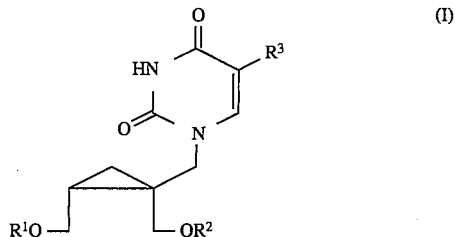

wherein $R^1$ and $R^2$, the same or different, are each a hydrogen atom, a $C_{1-6}$ acyl group or a $C_{1-6}$ acyl group substituted with a $C_{3-8}$ cycloalkyl group or $C_{6-8}$ aryl group; $R^3$ is an (E)-2-haloethenyl group; or a pharmaceutically acceptable salt thereof; and a pharmaceutically acceptable excipient, diluent or carrier.

10. The composition of claim 9, wherein said anti varicella zoster viral effective amount is 0.1 to 500 mg/kg/day.

11. A method of treating a patient with a varicella zoster virus comprising administering an anti-viral effective amount of a pharmaceutical composition comprising:

an anti-viral effective amount of a cyclopropane derivative of the formula (I):

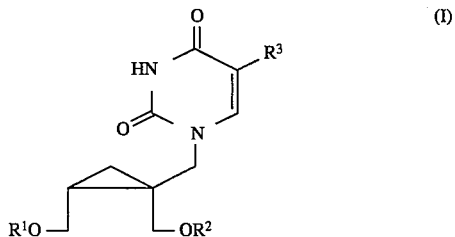

wherein $R^1$ and $R^2$, the same or different, are each a hydrogen atom, a $C_{1-6}$ acyl group or a $C_{1-6}$ acyl group substituted with a $C_{3-8}$ cycloalkyl group or $C_{6-8}$ aryl group; $R^3$ is an (E)-2-haloethenyl group; or a pharmaceutically acceptable salt thereof; and a pharmaceutically acceptable excipient, diluent or carrier.

* * * * *